United States Patent
Brogan et al.

(10) Patent No.: US 10,792,141 B2
(45) Date of Patent: Oct. 6, 2020

(54) SOFT TISSUE IMPLANT AND METHOD OF USING SAME

(75) Inventors: Cynthia M. Brogan, Cleveland Hts., OH (US); Cameron J. Fordyce, Bay Village, OH (US); Carl Michael Nilsson, Cleveland Hts., OH (US); Adam J. Zuch, Silver Lake, OH (US)

(73) Assignee: BLOCKHEAD OF CHICAGO, LLC, Chicago, IL (US)

( * ) Notice: Subject to any disclaimer, the term of this patent is extended or adjusted under 35 U.S.C. 154(b) by 0 days.

(21) Appl. No.: 13/250,622

(22) Filed: Sep. 30, 2011

(65) Prior Publication Data

US 2012/0259428 A1     Oct. 11, 2012

Related U.S. Application Data

(60) Provisional application No. 61/389,377, filed on Oct. 4, 2010.

(51) Int. Cl.
*A61F 2/02* (2006.01)
*A61B 17/80* (2006.01)
*A61F 2/00* (2006.01)
*A61F 2/28* (2006.01)

(52) U.S. Cl.
CPC .......... *A61F 2/0059* (2013.01); *A61F 2/2875* (2013.01)

(58) Field of Classification Search
CPC .... A61F 2/0063; A61F 2/0811; A61F 2/2803; A61F 2002/30133; A61F 2002/30233; A61F 2002/30281; A61F 2002/30357; A61F /

USPC .................... 623/17.17–17.19, 23.5
See application file for complete search history.

(56) References Cited

U.S. PATENT DOCUMENTS

| | | | |
|---|---|---|---|
| 4,778,472 A * | 10/1988 | Homsy et al. | 623/17.17 |
| 5,207,709 A | 5/1993 | Picha | |
| 5,348,788 A * | 9/1994 | White | 428/131 |
| 5,380,328 A * | 1/1995 | Morgan | 606/70 |
| 5,545,226 A * | 8/1996 | Wingo | A61F 2/2875 623/17.19 |
| 5,876,447 A * | 3/1999 | Arnett | 623/17.18 |
| 7,641,958 B2 * | 1/2010 | Berman | A61L 17/04 428/141 |
| 8,298,290 B2 * | 10/2012 | Pelissier et al. | 623/23.72 |
| 2001/0039454 A1 * | 11/2001 | Ricci et al. | 623/23.5 |
| 2002/0120338 A1 * | 8/2002 | Boyer, II | A61B 17/0401 623/17.19 |
| 2006/0224242 A1 | 10/2006 | Swords et al. | |

* cited by examiner

*Primary Examiner* — Ann Schillinger

(57) ABSTRACT

A soft tissue implant for correction of temporalis depressions or hollowing. The implant has a symmetric shape or external configuration, so that the device may be used as either a right or left temporalis implant. The implant may lie under or on top of the remaining temporalis muscle, or in the location formerly occupied by the temporalis muscle, to correct post-craniectomy temporal hollowing. The implant is manufactured from a medical grade, long term implantable silicone polymer material. The implant has a shell which forms the base of the device, with the base having an exterior surface and an interior surface with spaced projecting support structures. The implant is fully flexible or bendable.

12 Claims, 6 Drawing Sheets

SOFT TISSUE IMPLANT AND METHOD OF USING SAME

CROSS REFERENCE TO RELATED APPLICATIONS

The present application claims priority from U.S. Patent Application No. 61/389,377, having a filing date of Oct. 4, 2010, the entire disclosure of which is incorporated herein by reference.

TECHNICAL FIELD

The present application is directed to a soft tissue implant for reconstruction of soft tissue defects after craniotomy or craniectomy procedures, and specifically to a flexible silicone soft tissue implant which may be customized or used off the shelf during a surgical procedure.

BACKGROUND

A craniotomy is a surgical operation in which a bone flap is removed from the skull to access the brain. Craniotomies are often a critical operation performed on patients suffering from brain lesions or traumatic brain injury. Such surgical procedures are also conducted to allow doctors to surgically implant deep brain stimulators for the treatment of Parkinson's disease, epilepsy and cerebellar tremor. The location and amount of skull that needs to be removed depends to a large extent on the type of surgery being performed. In a craniotomy, the bone is replaced after access to the brain is completed.

Craniotomy is distinguished from craniectomy in which the skull flap is not replaced immediately. Decompressive craniectomy is an increasingly common neurosurgical procedure in which part of the skull is removed to allow a swelling brain with room to expand without being squeezed. It is performed on victims of traumatic brain injury and stroke.

The temporalis muscle is frequently impacted during craniotomy and craniectomy procedures. Post-surgical atrophy of the temporalis muscle is also common and results in facial depressions and headaches or jaw aches. A temporal depression, or temporalis depression, due to craniotomy or craniectomy is simply a depression formed in the location where the skull and/or soft tissue has been removed or a surgical procedure performed.

SUMMARY

The present application proposes the use of a soft tissue implant for correction of temporalis depressions or hollowing. The implant preferably has a shape or external configuration that is symmetric, so that the device may be used as either a right or left temporalis implant. The implant may lie under or on top of the remaining temporalis muscle, or in the location formerly occupied by the temporalis muscle, to correct post-craniectomy temporal hollowing. The implant is manufactured from a medical grade, long term implantable silicone polymer material, which is of a type well known in the art of surgical or cosmetic implants. The implant may be of any color, or clear material. The implant has a shell which forms the base of the device, with the base having an exterior surface and an interior surface with spaced projecting support structures. The implant shell is fully flexible or bendable. It should be understood that the durometer of any selected long term medical grade implantable material may also be adjusted to achieve the desired material hardness. The bendable nature of the implant enables it to fit any contours of the body which are presented. Additionally, the overall shape and size of the implant may be readily trimmed, for example using scissors during a surgical procedure, to accommodate smaller implant requirements for a semi-custom or custom fit.

The present implant shell or base includes an exterior surface which is substantially smooth to discourage adhesions. While a smooth surface may be desired to avoid adhesions, surface indents and/or shallow grooves may be provided in various directions. In one embodiment, two directions of exterior surface grooves are provided. The grooves in the exterior surface may be simulated striations similar to or along the lines of the temporalis muscle, such that the exterior surface of the implant has surface features substantially consistent with the soft tissue it replaces. Such surface features allow the soft tissue to grow into the surface features of the implant.

The interior surface of the shell is provided with spaced and flexible support structures which extend outwardly from the interior surface. In one embodiment, the support structures are a matrix or an array of spaced and contoured pillars which extend outwardly from the interior surface. Such pillars are positioned against the skull or temporalis muscle once implanted. Alternatively, arc-shaped ridges which are raised from the surface of the implant may be used as the spaced flexible support structures. It should be understood that such spaced flexible support structures projecting from the implant shell interior surface may be provided in various heights, widths, directions and combinations thereof.

DETAILED DESCRIPTION

Figure 1:
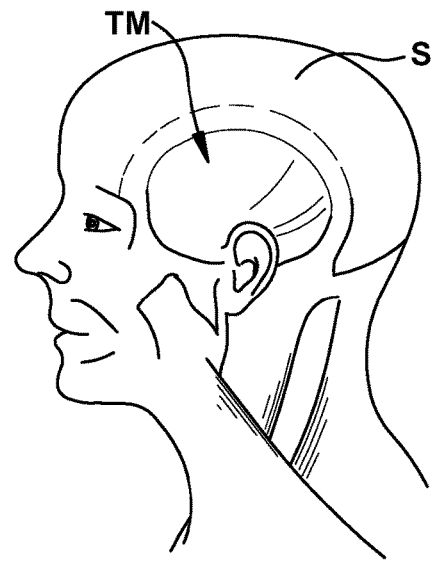
FIG. 1 is a diagram of the musculature, including the temporalis muscle, of the human skull.
Figure 2:
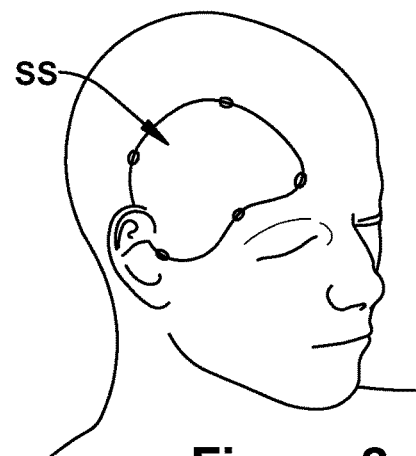
FIG. 2 is a diagram of the surgical site involved with a craniotomy or craniectomy surgical procedure.
Figure 3A:
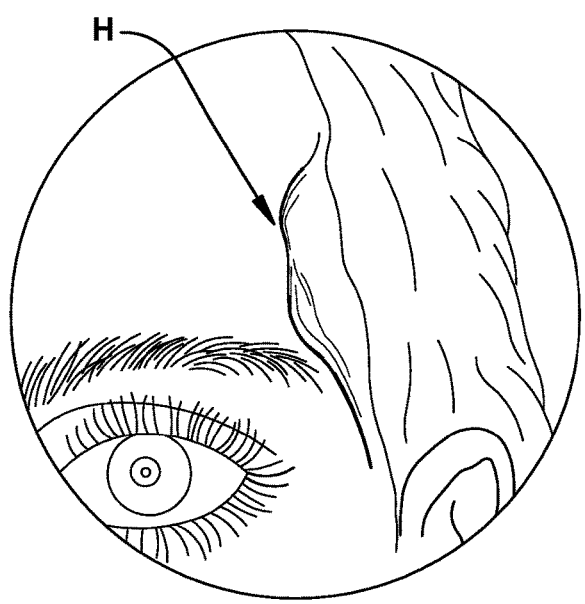
FIGS. 3A and 3B are respective before and after images, with FIG. 3A showing the hollowing effect or temporalis depression which may result following a surgical procedure impacting the temporalis muscle, and FIG. 3B showing the improved comesis resulting from the use of a soft tissue implant.
Figure 3B:
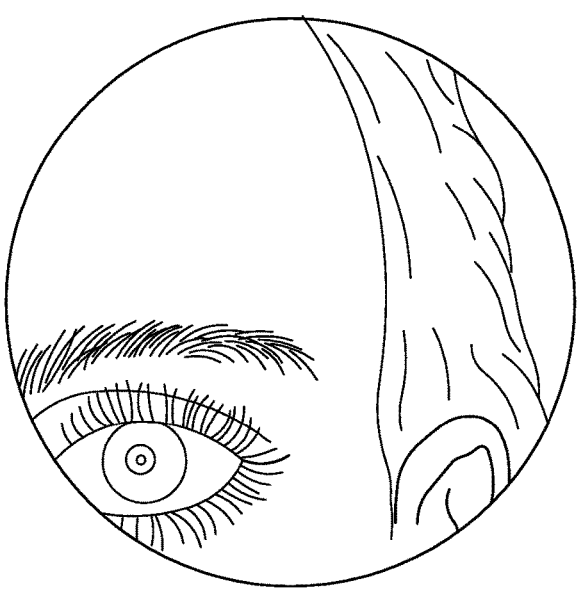
Figure 6:
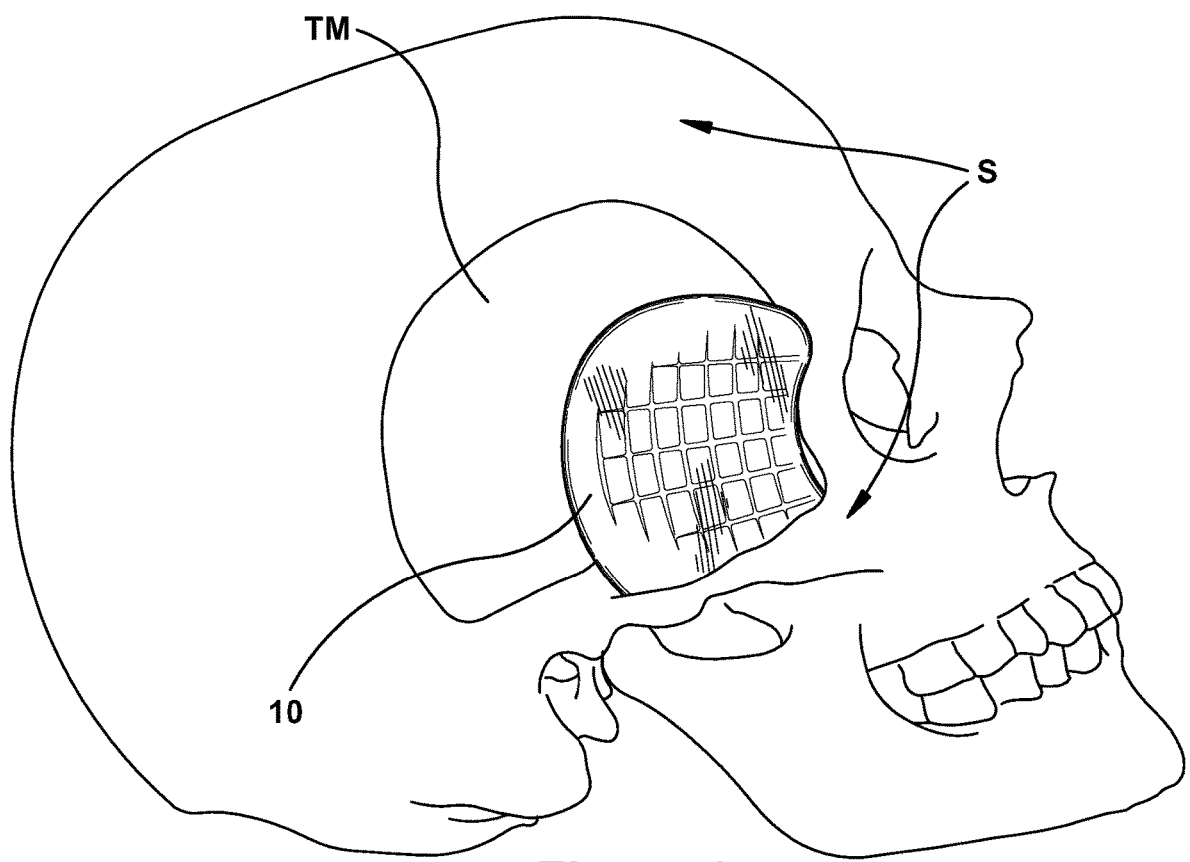
FIG. 6 illustrates a transparent embodiment of the soft tissue implant of the present application positioned within a skull and muscle model at the site of implant.
Figure 7A:
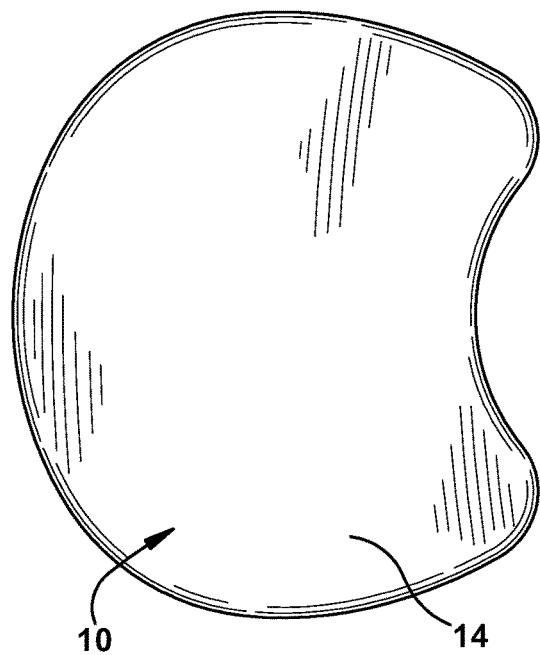
FIGS. 7A and 7B illustrate top and bottom views, respectively, of a non-transparent soft tissue implant of the present application.
Figure 7B:
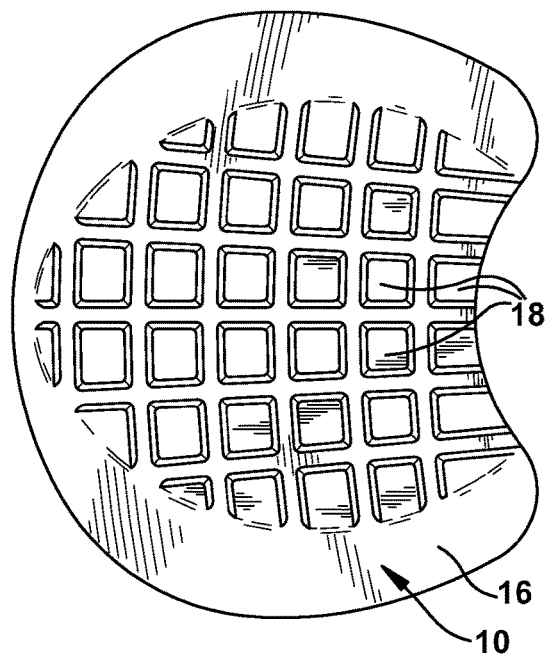

The present application is for a soft tissue implant 10 for correction of temporalis depressions which result from damage to the temporalis muscle, shown at TM in FIG. 1, during surgery conducted at the surgery site indicated generally at SS in FIG. 2. FIG. 3B illustrates the cosmetic improvement provided by an implant to correct the temporalis depression H shown in FIG. 3A. As shown in FIG. 6, the implant may lie under the skull bone S and on top of the remaining temporalis muscle TM, or in the location formerly occupied by the temporalis muscle, to correct post-craniectomy temporal hollowing H along the surgical site SS. The implant 10 may be placed at the time of the primary craniotomy or craniectomy surgical procedure, or can be placed after the primary surgery. In the event the implant is placed after the primary surgery, the implant can be provided as an outpatient procedure.

Figure 4:
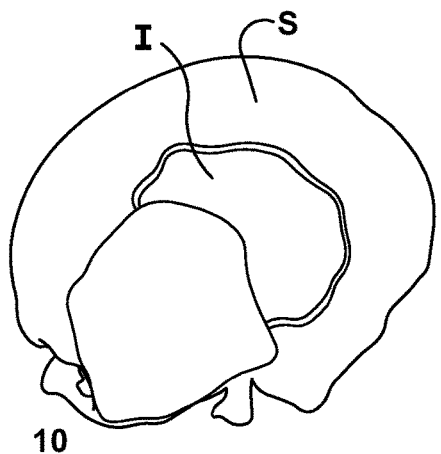
FIGS. 4 and 5 illustrate the use of a completely customized soft tissue implant, shown as non-transparent, used engaged with bone and an all plastic rigid implant, shown as transparent.
Figure 5:
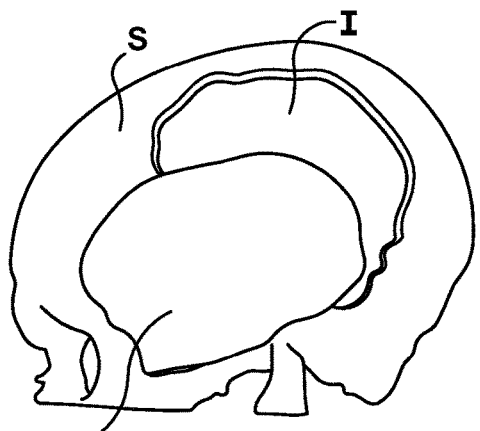

As shown in FIGS. 4 and 5, the implant 10 can be used in conjunction with a custom all plastic implant I, shown as a transparent component in FIGS. 4 and 5, where a customized soft tissue implant 10 is shown as non-transparent. Alternatively, the implant may be used in conjunction with bone, as schematically illustrated in FIGS. 4 and 5, where the soft tissue implant 10 is non-transparent and engaged with both bone S and a transparent bone implant I.

Figure 8A:
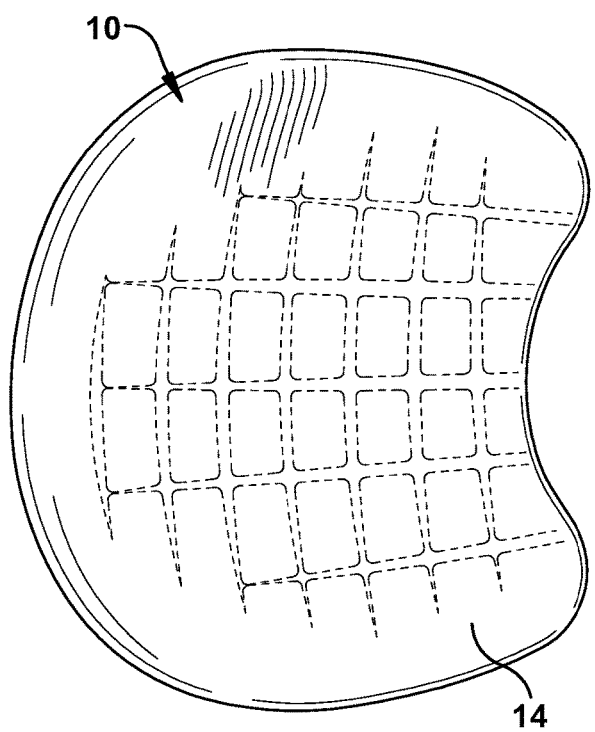
FIGS. 8A and 8B illustrate larger and smaller sizes, respectively, of a transparent soft tissue implant of the present invention.
Figure 8B:
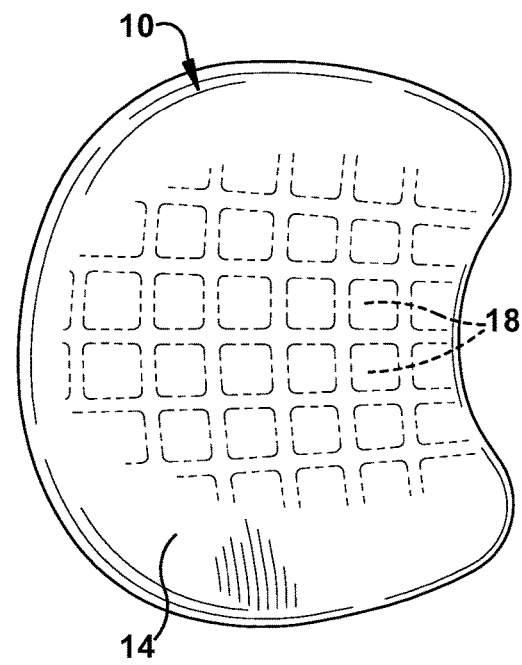
Figure 9:
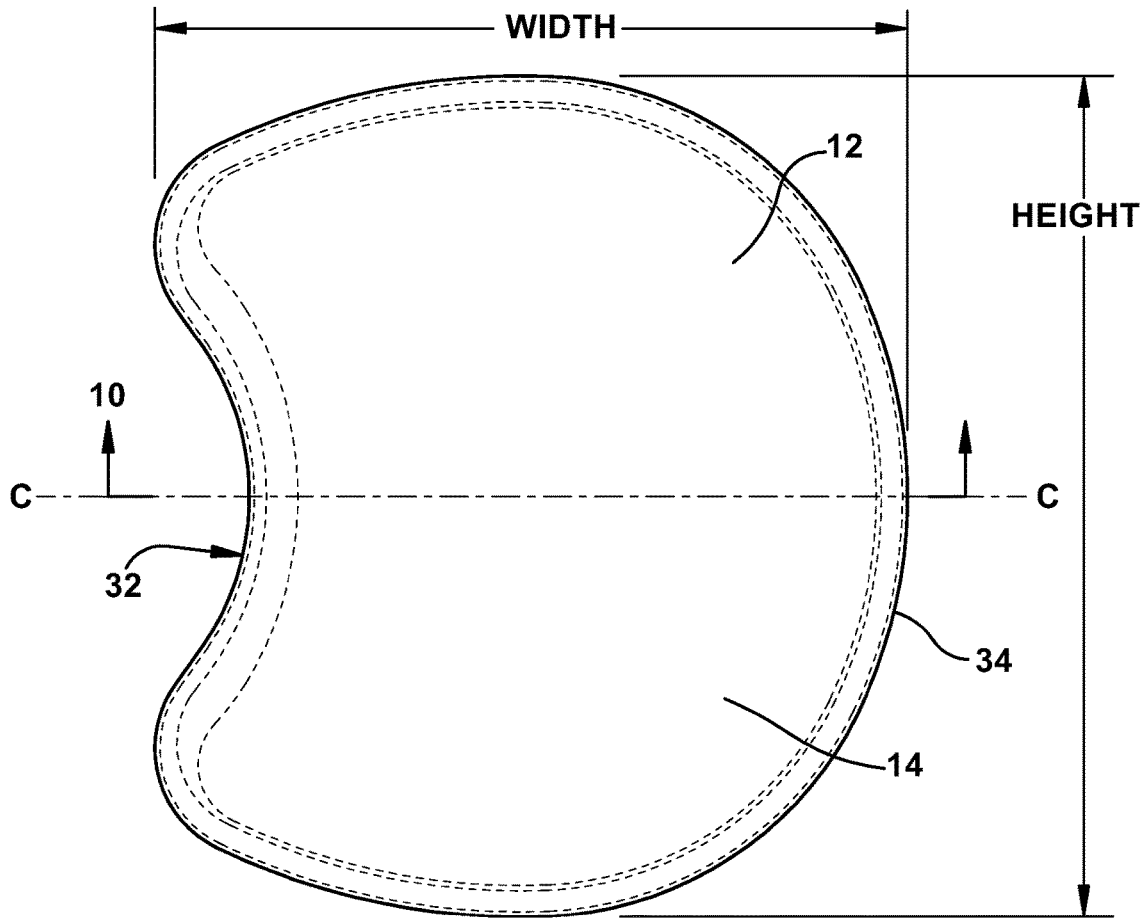
FIG. 9 is a schematic top view of a soft tissue implant of the soft tissue.

The implant 10 is provided with a shape or external configuration that is symmetric, so that the device may be used as either a right or left temporalis muscle implant. A central axis C, shown in FIGS. 9 and 11, illustrates the line of symmetry of the implants 10, 10'. Different overall shapes, such as the horseshoe or C shaped configuration of FIGS. 7A-10, and the clam shell configuration of FIGS. 11-14, are also illustrated. However various shapes and sizes may be provided to enable a semi-custom or "off the shelf" implant to be used as appropriate for an individual patient.

The soft tissue implants are also provided in different standardized sizes, as shown in FIGS. 8A, 8B and 12-13. The use of the present implant reduces wasted materials, since the desired implant size may be customized during the surgical procedure to ensure proper fit, instead of trying and then disposing of various ill-fitting custom implants until a desired fit is obtained. To further customize the implant, any edge or ridge of the implant may be trimmed at any location to achieve the desired configuration required for the implant during the surgical procedure. Such an implant optimizes efficiency and productivity during a single surgical procedure or multiple procedures.

The implant 10 is manufactured from a medical grade, long term implantable silicone polymer material, such as medical grade, long term implantable silicone polymer or rubber material, for example, having a durometer of between 25-50 hardness, for example from NuSil Technology, CA, USA, provides the implant with appropriate characteristics. It should be understood that any long term medical-grade implantable material would be sufficient. The polymer is mixed as prescribed, and the mixture is cast in a two-part mold to provide the resulting implant with the surface and structural characteristics described herein. The mixture is cured within the mold at the prescribed manufacturer recommended temperature. The implant may be of any color, or transparent as shown in FIG. 8A, 8B, where the transparency of the material enables the spaced projecting support structures 18 to be viewed through the exterior surface 14.

The implant 10 has a shell 12 which forms the base of the device, with the base 12 having an exterior surface 14 and an interior surface 16 with spaced projecting support structures 18. It is noted that where alternate embodiments of the implant are illustrated, duplicate components of the implant may be illustrated with a similar reference number, but with a prime designation.

Figure 15:
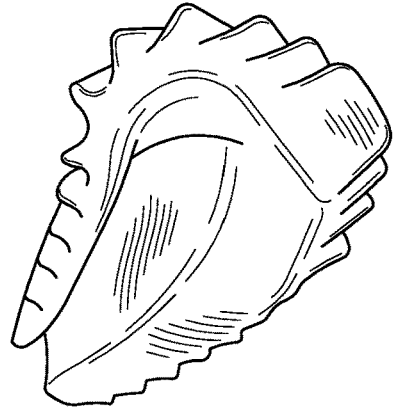
FIG. 15 illustrates the flexible bending of the soft tissue implant of the present application.
Figure 16:
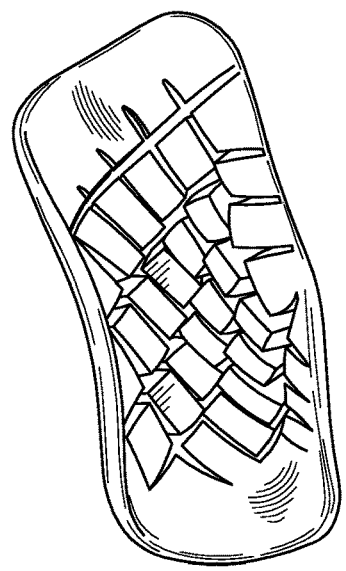
FIG. 16 illustrates the flexible bending of the soft tissue implant of FIGS. 7A and 7B, shown from the interior surface of the implant.

The implant shell 12 is fully flexible or bendable, as shown in FIGS. 15 and 16. It should be understood that the durometer of any selected implantable material may also be adjusted to achieve the desired material hardness. The bendable nature of the implant enables it to fit any contours of the body which are presented. Additionally, the use of such material enables the overall shape and size of the implant to be trimmed using scissors during a surgical procedure, to accommodate smaller implant requirements for a further customized fit.

Figure 10:
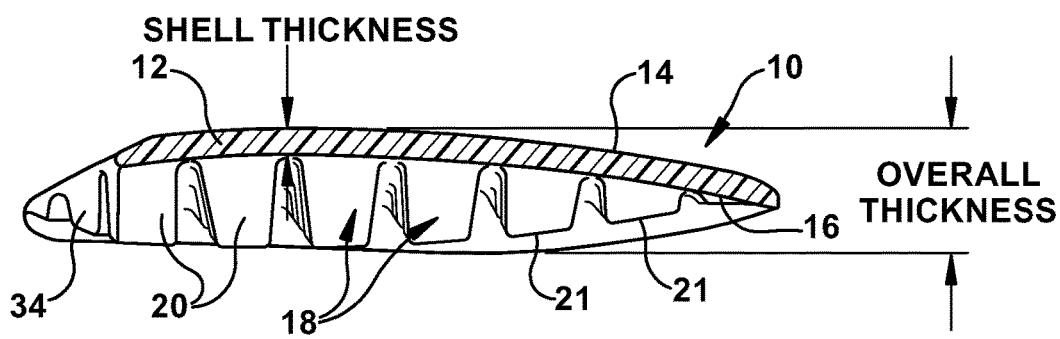
FIG. 10 is a schematic cut-away side view, taken along the line 10-10 of the soft tissue implant of FIG. 9.
Figure 11:
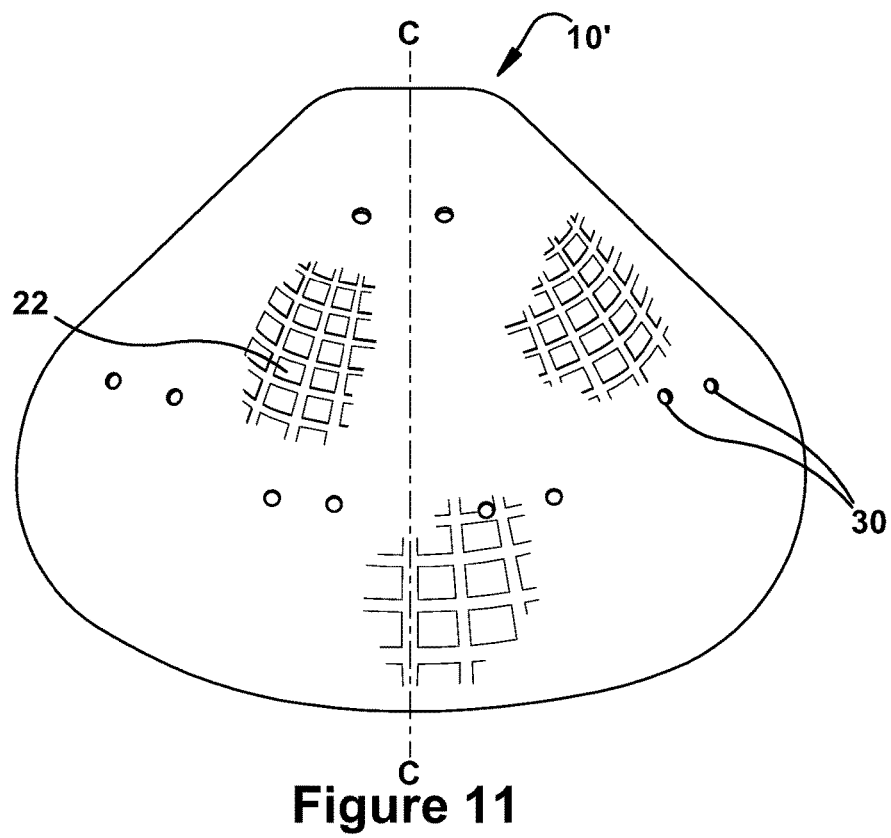
FIG. 11 illustrates an alternate embodiment of a soft tissue implant having a grooved exterior surface.

As shown in FIGS. 9-10, the shell 12 has a symmetric overall configuration and a curved configuration in cross section. The shell 12 has a concave portion 32 along one edge and a convex portion 34 along an opposite edge, such that the shell has overall horseshoe or C-shaped configuration. The projecting support structures 18 of FIGS. 7B, 8A, 8B and 10, extend outwardly from the interior surface 16 and are illustrated as contoured pillars arranged in a matrix of rows and columns having a slight curve. The contoured pillars 20 have varying heights and thicknesses, with taller pillars formed toward the center of the shell and shorter pillars formed along the outer edges of the shell. It should be understood that while the taller support pillars are relatively soft and not rigid, they are also less bendable than the shorter pillars, such that the flexibility of the shell 12 intermediate the pillars provides the desired conformability of the implant. As shown in FIG. 10, the varying heights of the pillars result in the top surfaces 21 of the pillars 20 form a curved plane of engagement with the skull or muscle once implanted. In an alternate embodiment of FIGS. 12-14, the projecting support structures 18 are ridges 24 formed by peaks 26 and troughs 28, with the peaks forming arcs in their overall configuration.

To demonstrate the overall size of the implant 12, the following sample measurements are provided for the small sized implant of FIG. 8B and the medium sized implant of FIG. 8A, with the height and width measurements given as shown in FIGS. 9 and 10:

| Length units in mm | HEIGHT | WIDTH | Shell Thickness | Overall Thickness |
|---|---|---|---|---|
| Small | 50.0 | 44.00 | 1.5 | 7.0 |
| Medium | 60.0 | 53.0 | 1.5 | 9.0 |
| Possible ranges | 20.0-120.0 | 15.0-100.0 | 0.5-5.0 | 5.0-50.0 |

Figure 12:
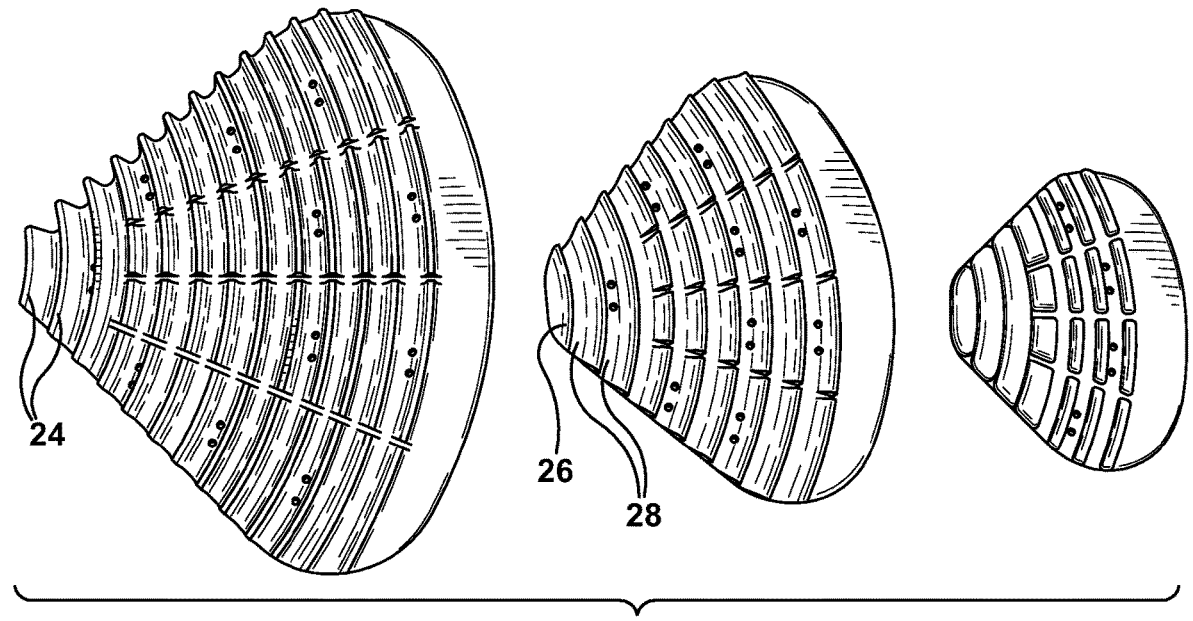
FIG. 12 illustrates three sizes of the alternate embodiment of the soft tissue implant of FIG. 11, shown from the interior surface.
Figure 13:
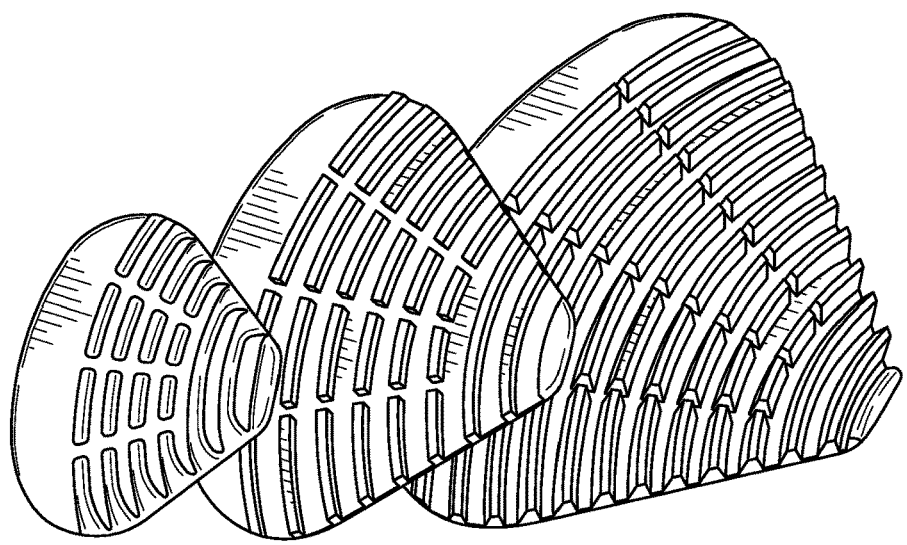
FIG. 13 illustrates three sizes of another alternate embodiment of the soft tissue implant.
Figure 14:
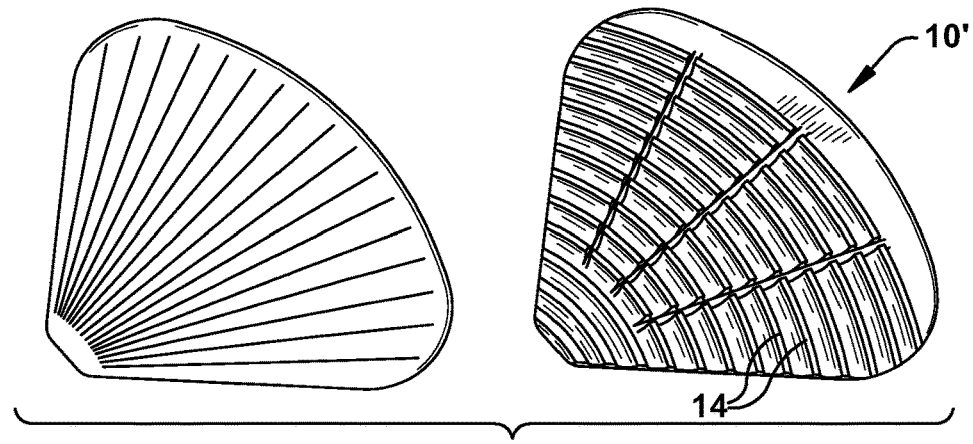
FIG. 14 illustrates the exterior and interior surface views of the alternate embodiment of the soft tissue implant of FIG. 13.

As shown in FIGS. 11 and 12 the implant is provided with holes 30 at various spaced locations through the shell 12 of the implant. In one embodiment, the numerous holes 30 are provided in pairs. The holes 30 enable sutures to be used to secure the implant in the desired position. Additionally, multiple single holes may be provided in various numbers, locations, orientations and spaced positions so that despite appropriate trimming of the implant for a customized fit, the implant still includes necessary holes for attaching the implant, and for tissue in growth.

While the invention has been illustrated and described in detail in the drawings and foregoing description, the description is to be considered as illustrative and not restrictive in character. Only the preferred embodiments, and such alternative embodiments deemed helpful in further illuminating the preferred embodiment, have been shown and described. It will be appreciated that changes and modifications to the foregoing can be made without departing from the scope of the following claims.

We claim:

1. A flexible polymer soft tissue temporal implant having a shell with a symmetric C-shaped overall configuration, a grooved exterior surface with spaced support structures having varying heights and thicknesses, where each support structure projects at an angle transverse to the shell, the projecting support structures are formed as peaks and troughs and are arced in their overall configuration, the shell of the flexible polymer soft tissue temporal implant has a curved configuration in cross section, and the flexible polymer soft tissue temporal implant is sufficiently flexible that the shell of the flexible polymer soft tissue temporal implant may be bent so that an edge of the grooved exterior surface touches along an opposite edge of the grooved exterior surface.

2. The flexible soft tissue implant of claim 1 wherein the projecting support structures are contoured pillars arranged in a matrix of rows and columns.

3. The flexible soft tissue implant of claim 2 having openings formed through the shell for use in securing the implant.

4. The flexible polymer soft tissue temporal implant of claim 1, wherein the shell has a concave portion along one edge and a convex portion along an opposite edge, providing the shell with the C-shaped overall configuration.

5. The flexible polymer soft tissue temporal implant of claim 1 having pre-formed openings formed in various numbers and spaced positions through the shell for use in securing the soft tissue temporal implant.

6. A soft tissue implant having a symmetric flexible polymer shell with a symmetric C-shaped configuration, the shell having a curved and grooved exterior surface with spaced tapered support structures attached thereto and extending therefrom at an angle transverse to the shell, the spaced tapered support structures have varying heights and thicknesses, and are formed as peaks and troughs which are arced in their overall configuration, and the shell is sufficiently flexible that the shell may be bent so that an edge of the curved and grooved exterior surface touches along an opposite edge of the curved and grooved exterior surface.

7. The soft tissue implant of claim 6, wherein the exterior surface has a substantially smooth configuration.

8. The soft tissue implant of claim 6, wherein the exterior surface has grooves formed therein.

9. The soft tissue implant of claim 6, wherein the spaced support structures are contoured pillars, with taller pillars formed toward the center of the shell and shorter pillars formed along the outer edges of the shell.

10. The soft tissue implant of claim 6, wherein the shell has a concave portion along one edge and a convex portion along an opposite edge, such that the shell has the symmetric overall C-shaped configuration.

11. A flexible polymer soft tissue implant having a symmetric flexible shell configuration, the shell having a symmetric C-shaped overall configuration and grooved exterior surface with spaced tapered support structures attached thereto and extending therefrom at an angle transverse to the shell, the spaced tapered support structures have varying heights and thicknesses, and are formed as peaks and troughs which are arced in their overall configuration, the shell is sufficiently flexible that the shell may be bent so that an edge of the curved and grooved exterior surface touches along an opposite edge of the curved and grooved exterior surface.

12. A method of using a silicone soft tissue implant comprising the steps of:

supplying a symmetrical flexible soft tissue implant having a symmetric C-shaped shell with holes therethrough, a grooved exterior surface and an interior surface having spaced support projections extending away from the interior surface for implantation at an angle transverse to the shell, the spaced support projections have varying heights and thicknesses, and are formed as peaks and troughs which are arced in their overall configuration, and the shell is sufficiently flexible that the shell may be bent so that an edge of the exterior surface touches along an opposite edge of the exterior surface;

cutting the edges of the soft tissue implant to fit the shape of the location where the implant is to be secured;

placing the support projections along the bone and tissue in the location where a temporalis muscle is normally located and the implant is to be secured; and securing the implant in the location where the implant is to be secured using the holes formed through the shell.

* * * * *